(12) United States Patent
Mecking et al.

(10) Patent No.: US 9,096,715 B2
(45) Date of Patent: Aug. 4, 2015

(54) POLYMERS MADE OF RENEWABLE RESOURCES

(75) Inventors: Stefan Mecking, Constance (DE); Dorothee Quinzler, Alpnach Dorf (CH)

(73) Assignee: BASF SE (DE)

( * ) Notice: Subject to any disclaimer, the term of this patent is extended or adjusted under 35 U.S.C. 154(b) by 354 days.

(21) Appl. No.: 13/575,155

(22) PCT Filed: Jan. 24, 2011

(86) PCT No.: PCT/EP2011/050924
§ 371 (c)(1),
(2), (4) Date: Oct. 15, 2012

(87) PCT Pub. No.: WO2011/089256
PCT Pub. Date: Jul. 28, 2011

(65) Prior Publication Data
US 2013/0030075 A1    Jan. 31, 2013

(30) Foreign Application Priority Data

Jan. 25, 2010  (DE) .......................... 10 2010 005 770

(51) Int. Cl.
| | | |
|---|---|---|
| *C08G 63/02* | (2006.01) | |
| *C08G 69/26* | (2006.01) | |
| *C07C 67/38* | (2006.01) | |
| *C08G 18/32* | (2006.01) | |
| *C08G 18/73* | (2006.01) | |
| *C08G 18/77* | (2006.01) | |
| *C08G 63/16* | (2006.01) | |
| *C08G 69/34* | (2006.01) | |

(52) U.S. Cl.
CPC .............. *C08G 69/265* (2013.01); *C07C 67/38* (2013.01); *C08G 18/3206* (2013.01); *C08G 18/3228* (2013.01); *C08G 18/73* (2013.01); *C08G 18/771* (2013.01); *C08G 63/16* (2013.01); *C08G 69/26* (2013.01); *C08G 69/34* (2013.01)

(58) Field of Classification Search
CPC .............................. C08G 63/78; C08G 63/178
USPC .................. 521/182, 184; 528/271, 272, 310; 560/204, 517
See application file for complete search history.

(56) References Cited

PUBLICATIONS

Biermann, et al. "Neue Synthesen mit Olen and Fetten als nachwachsende Rohstoffe fur die chemische Industrie" (2000) 112 pp. 2292-2310.
Carothers, "Polymers and Polyfunctionality" (1935) pp. 39-49.
Clegg, et al. "Highly active and selective catalysts for the production of methyl propanoate via the methoxycarbonylation of ethene" Chem. Commun. (1999) pp. 1877-1878.
Cornils, et al. "Applied Homogeneous Catalysis with Organometallic Compounds" Wiley-VCH, Weinheim, (2000) pp. 187-200.
Falbe, et al. "Rompp Chemie Lexikon" (1990) XP002638485, p. 1223.
Jimenez-Rodriguez, et al. "Dicarboxylic acid esters from the carbonylation of unsaturated esters under mild conditions" Inorganic Chemistry Communications (2005) pp. 878-881.
Jimenez-Rodriguez, et al., "Highly selective formation of linear esters from terminal and internal alkenes catalysed by palladium complexes of bis-(di-tert-butylphosphinomethyl)benzene" Chem. Commun. (2004) pp. 1720-1721.
Translation of International Preliminary Report on Patentability for PCT/EP2011/050924.
Zeidler, et al. "Uber das Spreiten von Lipiden auf der Haut" (1985) pp. 403-408.

*Primary Examiner* — Terressa Boykin
(74) *Attorney, Agent, or Firm* — Drinker Biddle & Reath LLP

(57) ABSTRACT

Polycondensates with long-chain linear methylene sequences, their production, a method for producing linear odd-numbered $C_{>20}$ α,ω-dicarboxylic acids and derivatives thereof and applications of the polycondensates are described.

6 Claims, No Drawings

POLYMERS MADE OF RENEWABLE RESOURCES

RELATED APPLICATIONS

This application is a national stage application (under 35 U.S.C. §371) of PCT/EP2011/050924, filed Jan. 24, 2011, which claims benefit of German application 10 2010 005 770.3, filed Jan. 25, 2010.

The invention relates to polycondensates having relatively long linear methylene sequences in the main chain, to methods for their production, to the use thereof and to a catalytic method for producing the monomers.

Renewable resources are of interest as alternatives to finite fossil resources. Moreover, new types of materials with advantageous properties may be accessible therewith. For this, it is desirable for the molecular structure of the resource to also be reflected in the structure of the resulting products.

An attractive characteristic of vegetable oils and fats is the linear hydrocarbon structure of the fatty acids present (in the form of the triglycerides). This has been utilized for a long time for producing the technical plastic polyamide-11 starting from ricinoleic acid. In this case, however, only part of the fatty acid molecule is used. The thermal rearrangement of ricinoleic acid leads, with the cleavage of the fatty acid chain, to undec-10-enoic acid, which is further reacted to give the polyamide-11, as well as heptanal as by-product. Moreover, the underlying rearrangement reaction requires the presence of the hydroxy group neighboring the double bond and is therefore limited among the fatty acids that are currently industrially available to ricinoleic acid and derivatives thereof. Also accessible from ricinoleic acid is sebacic acid, which is reacted to give polycondensates such as polyamide-6,10. In this case, 2-octanol is formed as by-product.

A complete linear integration of long-chain $C_{>20}$ fatty acids into polymers is desirable since, in so doing, firstly the substrate would be utilized entirely in material terms for building up the polymers, and secondly long linear methylene sequences can lead to desirable properties such as crystallinity and, associated therewith, melting and crystallization points, mechanical and other application properties, mixing behavior in polymer blends, or a low water absorption. By means of dimerization, fatty acids can be converted to the so-called dimer fatty acids, although these have a branched, non-linear structure and lead to non-crystalline segments (Angew. Chem. 2000, 112, 2292). A complete linear integration of fatty acids into monomers and polymers produced therefrom is difficult to realize since the reactive double bond of unsaturated fatty acids is located in the middle of the molecule and the terminal methyl group is not very reactive.

When reacting resources from renewable sources, it should generally be taken into consideration that these in most cases comprise impurities which can disturb reaction processes and lead to product mixtures instead of pure substances. Different fatty acids or derivatives thereof often have a different spectrum of impurities depending for example on their biological origin.

Moreover, most of the synthesis processes for relatively long-chain, α,ω-dicarboxylic acids or derivatives thereof lead, irrespective of their practicability and the nature and availability of the starting substances, to the even-numbered products.

The catalytic alkoxycarbonylation of olefins, i.e. the reaction with carbon monoxide and an alcohol, is a known reaction for producing esters (Applied Homogeneous Catalysis with Organometallic Compounds, Ed. B. Cornils and W. A. Herrmann, Wiley-VCH, Weinheim, 2000). Thus, the cobalt-catalyzed reaction of methyl esters of monounsaturated fatty acids lead unselectively to 60:40 mixtures of the linear α,ω-dicarboxylic acid dimethyl ester and branched diesters (Fette, Seifen, Anstrichmittel 1985, 87, 403). For the methoxycarbonylation of ethylene, it has been found that a palladium(II) catalyst modified by 1,2-bis[(di-tert-butyl-phosphino)methyl]benzene is particularly highly suitable (Chem. Commun. 1999, 1877). Notably, these catalysts also convert internal olefins, such as 4-octene, to the linear methyl esters (Chem. Commun. 2004, 1720). The analogous reaction in methanolic solution of the internally unsaturated $C_{18}$-fatty acid methyl ester methyl oleate, and also of the polyunsaturated analogs methyl linolate and methyl linolenate, leads preferentially to the saturated α,ω-dicarboxylic acid ester, 1,19-dimethyl-nonadecanedioate (Inorg. Chem. Commun. 2005, 8, 878). However, this has not been obtained in the purity required for producing polycondensates (Trans. Faraday Soc. 1936, 32, 39).

Erucic acid is one example of an unsaturated readily available $C_{>20}$ fatty acid. The reaction of methyl erucate with carbon monoxide in methanol with trialkyldiphosphine-modified palladium(II) catalyst has proven to be problematic; no satisfactory alkoxycarbonylation was observed. Surprisingly, however, it has been found that with erucic acid and other unsaturated fatty acids having more than twenty carbon atoms ($C_{>20}$ fatty acids) in higher alcohols, the reaction takes place selectively to give α,ω-dicarboxylic acid esters and these are obtained in purities of >99%.

Furthermore, it has been found that the corresponding α,ω-dicarboxylic acids and esters thereof, and also their reduced hydroxy and amino derivatives are suitable in an exceptional manner as monomers for producing polycondensates.

The invention therefore provides a polycondensate comprising one or more repeat units of the formula (I),

in which the symbols and indices have the following meanings:

Z, Z' is identical or different and is —X—C(=O)~, —C(=O)—HN—CH$_2$~, —C(=O)—O—CH$_2$~, —NH—C(=O)—O—CH$_2$~, —O—C(=O)—NH—CH$_2$~;

X is O or NH;

~ indicates the bond to the group (CH$_2$)$_{2n+1}$ and n is a number ≥10.

The invention further provides a method for producing the polycondensate according to the invention, where at least one monomeric compound of the formula (II)

in which $Z^1$, $Z^{1'}$ is ~C(=O)-Q or —CH$_2$—NCO;

Q is identical or different and is OH, halogen or $C_1$-$C_{10}$-alkoxy;

~ indicates the bond to the group (C$_2$)$_{2n+1}$ and n is a number ≥10, is polycondensed with at least one di- or polyol or at least one di- or polyamine, and/or at least one monomeric compound of the formula (III),

in which $Z^2$, $Z^{2'}$ is identical or different and is HO—CH$_2$~ or H$_2$N—CH$_2$~;

~ indicates the bond to the group (CH$_2$)$_{2n+1}$ group and n is a number ≥10, polycondensed with at least one di- or polycarboxylic acid, a reactive derivative of such a di- or polycarboxylic acid or at least one di- or polyisocyanate.

The invention further provides the use of the polycondensate according to the invention in moldings, coatings, foams, films, foils and/or fibers, and the corresponding objects which comprise the polycondensate according to the invention.

The invention likewise provides a method for producing saturated or unsaturated α,ω-dicarboxylic acids or esters having in each case 2n+3 carbon atoms in the acid moiety, where n is ≥10, comprising the step of a hydroxy- or alkoxycarbonylation of a mono- or polyunsaturated fatty acid ester having 2n+2 carbon atoms in the acid moiety, where n is ≥10, in the presence of a catalyst comprising at least one palladium compound and at least one phosphane, at a temperature in the range from 50 to 120° C. and a pressure from 3 to 80 atm.

The monomers for producing the polycondensates according to the invention are obtained according to the invention by hydro- or alkoxycarbonylation of unsaturated fatty acids having at least 22 carbon atoms. The reaction takes place in the presence of a catalyst.

The catalyst used is one which comprises a palladium compound and at least one phosphorus-containing ligand which can coordinate to the metal center via one or more phosphorus atoms. In the phosphorus-containing ligand, suitable substituents $R'''^1$-$R'''^3$ on the phosphorus atom $PR'''^1R'''^2R'''^3$, independently of one another, are identical or different and are H, open-chain or cyclic aliphatic radicals $C_1$ to $C_{30}$, aromatic radicals $C_1$ to $C_{30}$, in particular $C_5$-$C_{12}$, and also open-chain or cyclic aliphatic radicals $C_1$ to $C_{30}$ and aromatic radicals $C_1$ to $C_{30}$, in particular $C_5$-$C_{12}$, bonded via heteroatoms such as N, O or S. The radicals $R'''^1$ to $R'''^3$ can also comprise heteroatoms in the side chain, such as, for example, O, N, S or P. Particularly suitable radicals are tert-butyl groups. The ligand can comprise two or more phosphorus atoms which are bridged via one or more of the radicals R'''. Particularly suitable bridging radicals are those which bridge the phosphorus atoms via three or four atoms. Particularly suitable bridging radicals are —$CH_2$—$C_6H_4$—$CH_2$— and —$(CH_2)_3$—.

Preferably, phosphanes are used. Particular preference is given to using trialkyl-phosphanes and bidentate phosphanes. Examples of suitable phosphorus-containing ligands are: 1,3-bis(di-tert-butylphosphino)propane; 1,3-bis(di-tert-butylphosphino)butane; 1,3-bis(di-tert-butylphosphino)-2,2'-dimethylpropane; 1,2-bis[(di-tert-butylphosphino)methyl]benzene; 1,2-bis(cyclooct-1,5-diylphosphino)methypenzene; 1,3-bis(cyclooct-1,5-diylphosphino)propane; 1-[(di-tert-butylphosphino)methyl]-2-(di-tert-butylphosphino)benzene.

It is possible to use one sort of phosphorus-containing ligand or a mixture of two or more phosphorus-containing ligands.

Examples of suitable palladium compounds are palladium acetate, palladium hexanoate, palladium octanoate, bis(dibenzylideneacetone)palladium, tetrakis(tri-phenylphosphane)palladium, (1,5-cyclooctadiene)dimethylpalladium, (1,5-cyclo-octadiene)dichloropalladium, (1,5-cyclooctadiene)methylchloropalladium, tetrakis-(acetonitrile)palladium (II) tetrafluoroborate and diacetonitriledichloropalladium.

The catalyst optionally comprises further components, for example organic and/or inorganic acids and/or salts thereof. Suitable further components which may be mentioned by way of example are trifluoromethanesulfonic acid, methanesulfonic acid, perchloric acid, p-toluenesulfonic acid, $[H(OEt_2)][BAr^F_4]$, $NaBAr^F_4$ where $Ar^F$=3,5-bis(trifluoromethyl)phenyl.

The catalyst components can be mixed together in any desired order. The mixing can take place in or outside of the reaction vessel for the carbonylation. In particular, preformed palladium complexes of phosphane can be used. Examples are $[(diphosphine)PdX_2]$ where X=methanesulfonate, trifluoromethanesulfonate, or tosylate.

A particularly suitable catalyst is a combination of a palladium(II) salt and 1,2-bis[(di-tert-butylphosphino)methyl]benzene, in particular in combination with methanesulfonic acid.

The molecular ratio of palladium(II) compound to phosphorus in the phosphane ligand is generally from 1:0.5 to 1:100, preferably from 1:0.5 to 1:20, particularly preferably from 1:2 to 1:10.

The molecular ratio of Pd(II) compound to the optionally present acid is optionally from 1:0.5 to 1:200.

The alcohols required for the alkoxycarbonylation are suitable as reaction medium. Preference is given to $C_2$-$C_{36}$ alcohols, such as ethanol, n-propanol, isopropanol, n-butanol, isobutanol, t-butanol, pentanol, hexanol, heptanol, n-octanol, isooctanol, 2-ethylhexanol, cyclohexanol, 2-phenylethanol, phenol, and benzyl alcohol or mixtures. Additionally suitable are aprotic organic solvents such as methylene chloride, chloroform, dichloroethane, benzene, toluene, chloro-benzene, isobutane, hexane, heptane, octane, diethyl ether, diphenyl ether, tetrahydrofuran, 2-methyltetrahydrofuran, sulfolane, N-methylpyrrolidone, dimethylacetamide, acetone, cyclohexanone, triethylamine, tributylamine, and mixtures of these compounds. The reaction medium can generally comprise up to 50% by volume of methanol, preferably less than 20% by volume of methanol. The reaction mixture can be anhydrous or comprise water. To produce the α,ω-dicarboxylic acids used according to the invention by means of hydrocarbonylation, the presence of water is necessary. If, for producing α,ω-diesters, an alkoxycarbonylation is carried out, the reaction mixture is preferably anhydrous.

Furthermore, the fatty acid ester used can also serve as reaction medium. The reaction mixture can be single-phase or multi-phase. Preferably, the reaction mixture consists of just one liquid phase. During the reaction, reaction medium, reagents and catalyst or catalyst components can be optionally added continuously or in a pulsed manner.

The temperature of the reaction mixture is in the range from −10° C. to +200° C., preferably in the range from +50° C. to 120° C., particularly preferably in the range from 85° C. to 100° C. The pressure during the reaction is in the range from 0.1 to 200 atm, preferably 3 to 80 atm, particularly preferably 10 to 40 atm.

The substrate used is esters of mono- or polyunsaturated fatty acids having an even number of carbon atoms in the acid moiety, which is greater than 20 and preferably not greater than 34. The symbol n in the formulae therefore stands for a natural number. Preference is given to mono- or poly-, particularly preferably monounsaturated fatty acid esters having 22, 24, 26, 28, 30, 32 or 34 carbon atoms (in the acid moiety), particularly preferably 22, 24 or 26 carbon atoms, in particular 22 carbon atoms. Optionally, the free acids can also be used. Preferred esters of these fatty acids are esters of monofunctional alcohols, particularly preferably $C_1$-$C_{10}$-alkyl esters.

Of particular suitability are esters of erucic acid (cis-13-docosenoic acid), in particular the ethyl ester.

Substrates which can be used are esters of pure $C_{>20}$-fatty acids or technical-grade $C_{>20}$ fatty acid esters which comprise, inter alia, polyunsaturated fatty acid esters. Although esters of monofunctional alcohols are preferred, the use of esters of polyfunctional alcohols, for example of triglycerides, is also possible.

Preference is given to the use of fatty acids and esters thereof from natural sources, for example from plant oils. For obtaining esters of erucic acid, particular preference is given to the seeds of erucic acid-containing rapeseed and seakale varieties, for example Abyssinian seakale.

The molar ratio of the fatty acid ester, preferably erucic acid ester, to the molar amount of palladium in the catalyst used according to the invention is generally 10 000 000:1 to 10:1, preferably 1 000 000:1 to 100:1, particularly preferably 10 000:1 to 500:1.

When using esters of even-numbered fatty acids, the carbonylation of $C_{>20}$ fatty acid esters leads to esters of uneven-numbered linear $C_{>21}$ α,ω-dicarboxylic acids.

The α,ω-dicarboxylic acids produced according to the invention and esters thereof are suitable as monomers for producing polycondensates according to the invention.

Also suitable are reactive derivatives of these acids, such as acid halides, activated esters, anhydrides or imidazolides.

Likewise suitable, for example in combination with the diacids or diesters, are the corresponding α,ω-diols, which are obtained from the diacids/diesters by known reduction processes with which the person skilled in the art is familiar.

Using known methods for the reduction of carboxylic acid derivatives to alcohols, it was possible, for example, to convert 1,23-diethyltricosanedioate to >99% pure 1,23-dihydroxytricosane. Examples of suitable methods for reducing carboxylic acids or derivatives thereof to give alcohols are catalytic hydrogenation with hydrogen, reduction by means of inorganic hydridic reagents, and reduction by organic compounds with oxidation of the same.

Furthermore, the α,ω-dicarboxylic acids produced according to the invention and esters thereof, and also the α,ω-diols obtainable therefrom, can be converted by known methods with which the person skilled in the art is familiar to give the corresponding α,ω-diamines, which in turn can be used as monomers in the synthesis of polycondensates according to the invention. Known processes, specified by way of example, for converting carboxylic acids or esters thereof to amino groups are amidation, followed by elimination of water, and hydrogenation; for converting alcohols to amines, halogenation or tosylation, followed by reaction with ammonia or alternatively conversion to the azide followed by reduction. To produce diisocyanates, the amines can be reacted with phosgene or phosgene equivalents.

Esters of linear uneven-numbered $C_{\geq 23}$ aliphatic α,ω-dicarboxylic acids, and linear uneven-numbered $C_{\geq 23}$ aliphatic α,ω-diols can be converted to polymers which are provided by the invention. The diesters here can be used as they are or in activated form, for example as acids, as chlorides, or anhydrides. Preferably, for the conversion to polymers, 1,23-tricosanedicarboxylic acid or esters thereof, 1,23-tricosanediol, 1,23-tricosanediamine and 1,23-tricosanediisocyanate are used. Particularly preferably, 1,23-tricosanedicarboxylic acid or esters thereof are used.

Besides at least one of the α,ω-difunctional compounds obtainable according to the invention and detailed in the preceding paragraph, further polyfunctional alcohols, amines, acids or esters, chlorides or anhydrides thereof, cyclic lactams or lactones, and isocyanates can also be used in the production of the polymers according to the invention. Besides the specified functional groups, these can also comprise further heteroatoms. Examples of suitable alcohols are ethylene glycol, 1,3-propanediol, 1,2-propanediol, 1,4-butanediol, cyclohexanediol, 1,6-hexanediol, 1,10-decanediol, 1,12-dodecanediol, 1,18-octadecanediol, 1,19-nonadecanediol, 2,2-di(4-hydroxyphenyl)propane, diethylene glycol, dihydroxy-terminated polyethylene glycol and trimethylolpropane, and also aromatic di- and polyhydroxy compounds, such as 4,4'-dihydroxybiphenyl and bisphenols such as bisphenol A and bisphenol AF. Examples of suitable amines are ethylenediamine, diethylene triamine, 1,2-diaminopropane, 1,3-diaminopropane, 1,4-diaminobutane, 1,5-diaminopentane, 1,6-diaminohexane, 1,10-diaminodecane, 1,12-diaminododecane, and also aromatic diamines such as p-phenylenediamine. Examples of suitable carboxylic acids are maleic acid, succinic acid, fumaric acid, adipic acid, sebacic acid, 1,19-nonadecanedioic acid, phthalic acid, terephthalic acid. Examples of suitable lactams are ε-caprolactam, lauryllactam. Examples of suitable lactones are ε-caprolactone and butyrolactone. Examples of suitable diisocyanates are hexamethylene diisocyanate and 4,4'-diphenylmethane diisocyanate.

Preferably, 1,23-tricosanedicarboxylic acid or esters thereof of monofunctional alcohols is reacted, in the presence or absence of further dicarboxylic acids or esters thereof specified by way of example in the preceding paragraph, with one or more diols, diamines, optionally in the presence of lactams. Suitable diols, diamines and lactams are specified by way of example in the preceding paragraph.

1,23-Tricosanedicarboxylic acid is particularly preferably polycondensed with one or more of the following compounds: ethylene glycol, 1,3-propanediol, 1,4-butanediol, cyclohexanediol, 1,6-hexanediol, 1,10-decanediol, 1,12-dodecanediol, 1,18-octadecanediol, 1,19-nonadecanediol, 1,23-tricosanediol, 2,2-di(4-hydroxyphenyl)propane, diethylene glycol, dihydroxy-terminated polyethylene glycol, ethylenediamine, diethylenetriamine, 1,3-diaminopropane, 1,4-diaminobutane, 1,5-diaminopentane, 1,6-diaminohexane, 1,10-diaminodecane, 1,12-diaminododecane, 1,23-tricosanediamine.

Likewise particularly preferably, the α,ω-dicarboxylic acid used according to the invention, preferably 1,23-tricosanedicarboxylic acid, is polycondensed together with succinic acid, adipic acid and/or terephthalic acid with one or more of the following compounds: ethylene glycol, 1,3-propanediol, 1,4-butanediol, cyclohexanediol, 1,6-hexanediol, 1,10-decanediol, 1,12-dodecanediol, 1,18-octadecanediol, 1,19-nonadecanediol, 1,23-tricosanediol, 2,2-di(4-hydroxyphenyl)-propane, diethylene glycol, dihydroxy-terminated polyethylene glycol, ethylenediamine, diethylenetriamine, 1,3-diaminopropane, 1,4-diaminobutane, 1,5-diaminopentane, 1,6-diaminohexane, 1,10-diaminodecane, 1,12-diaminododecane, 1,23-tricosanediamine.

Polymerization processes are sufficiently known to the person skilled in the art. The polymerization can take place in the presence or absence of catalysts, solvents, suspension agents or other additives. The polymerization can take place for example in solution, melt, suspension, non-aqueous dispersion or aqueous dispersion. Suitable catalysts are, for example, organic or inorganic acids; and also alkoxides, carboxylates and oxides of transition metals or main group metals. The polymerization takes place at a pressure of 0.00001 mbar to 100 bar. To remove volatile by-products, the polymerization can take place in vacuo. The polymerization mixture can be force-mixed, for example by means of stirrers or extruders. The polymerization can take place in one or more stages.

Optionally, crosslinking can take place during or after the polymerization by means of suitable reagents. As a result of this, certain properties, for example elasticity or flow properties, can be attained or improved.

Furthermore, the properties of the polycondensates according to the invention can be modified by chain extension, for example by reaction with carbonylbiscaprolactam (CBC) and/or phenylene-1,4-bis-oxazoline (1,4-PBO). Further suitable methods of chain extension are, for example, the reaction with polyfunctional isocyanates. The polymers according to the invention can be used as prepolymers in polycondensations and polyadditions. For example, dihydroxy-terminated polymers according to the invention can be reacted with polyfunctional isocyanates or carboxylic acids.

In a preferred embodiment, the group Z, Z' in the formula (I) correspond to —X—C(=O)— or —X'—C(=O)—, where X, X' are identical or different, preferably identical, and are O or NH, preferably O.

This embodiment relates to polycondensates comprising repeat units —X—C(=O)—$(CH_2)_{2n+1}$—C(=O)—X'— where n≥10 and X, X' is O or NH.

Furthermore, preference is given to polycondensates in which Z is a group —C(=O)—O—$CH_2$—, —C(=O)—NH—$CH_2$—, —NH—C(=O)—O—$CH_2$— or —O—C(=O)—NH—$CH_2$~, i.e. polycondensates comprising repeat units -M-$(CH_2)_{2n+3}$-M'—, where n is ≥10 and M, M' are an amide, ester or urethane function.

Preference is also given to copolyesters which, besides a monomer according to the invention, comprise further monomers, preferably polyesters [{-$A^1$-OC(=O)—$(CH_2)_{2n+1}$—C(=O)O—}$_x${-$A^1$-OC(=O)-$A^2$-C(=O)O—}$_y$], where n is ≥10 and $A^1$, $A^2$ are a $C_2$ to $C_{36}$ aliphatic, cycloaliphatic, aromatic or mixed radical. A mixed radical is, for example, an araliphatic group. x and y refer in each case to the mole fraction, i.e. x+y=1.

Preference is likewise also given to copolyamides which, besides a monomer according to the invention, have further monomers, in particular polyamides [{-$A^3$-NHC(=O)—$(CH_2)_{2n+1}$—C(=O)NH—}$_x${-$A^3$-NHC(=O)-$A^4$-C(=O)NH—}$_y$], where n is ≥10 and $A^3$, $A^4$ are in each case an aliphatic, cycloaliphatic, aromatic or mixed radical having 2 to 36 carbon atoms.

Preference is also given to polyesters and polyamides according to the invention where y=0.

Furthermore, preference is given to polycondensates according to the invention where n=10, in which at least some of the monomers are derived from 1,23-tricosanedicarboxylic acid.

The polymers according to the invention comprise in general at least 1 mol %, preferably at least 10 mol %, particularly preferably 50 mol %, of at least one type of the repeat units of the formula (I), preferably of the repeat units —X—C(=O)—$(CH_2)_{2n+1}$—C(=O)—X'— or -M-$(CH_2)_{2n+3}$-M'—; where n≥10, where X, X', independently of one another, are identical or different and are O or NH; M, M', independently of one another, are identical or different and are an amide, ester or urethane function.

The polycondensates according to the invention, in particular polyesters, generally have a number-average molecular weight $M_n$ of from 1000 to 2 000 000 s/mol, preferably from 5000 to 200 000 g/mol and particularly preferably from 10 000 to 50 000 g/mol.

An advantage of the polycondensates according to the invention, in particular polyesters, is firstly that they can be produced on the basis of renewable materials, for example erucic acid esters, based on, for example, seakale. A further advantage of the polycondensates according to the invention, in particular polyesters, is that they are fundamentally suitable as biodegradable polymers. In this connection, within the context of the invention, biodegradable polymers is the term used to refer to those materials which are degraded by microorganisms, enzymes or hydrolysis, for example in the soil. The biodegradability is tested by means of the DIN standard EN 13432. The biodegradable materials have to be degraded within 6 to 10 weeks in a large-scale composting system. In a further embodiment, the invention thus relates to a polyester according to the invention which is biodegradable. As a result of the long-chain crystalline segments, melt and crystallization properties are influenced in a desirable way and are sufficiently high for thermoplastic processing. On account of their crystallinity, polyesters according to the invention exhibit correspondingly high melting and crystallinity points which can be for example $T_m$>80° C. and $T_c$>70° C., in particular $T_m$>90° C. and $T_c$>75° C. Furthermore, the systems exhibit a low water absorption.

The polymers according to the invention can be used advantageously in numerous applications, for example in moldings, coatings, foams, films, foils and fibers. The polymers according to the invention can also be used in mixtures with other plastics.

Methods for processing the polymer according to the invention which may be mentioned by way of example are injection molding, coextrusion, foil casting, blow molding, foil blowing, calendering, melt pressing, wet spinning, dry spinning, melt spinning, deep drawing, powder coating and coating from organic solution or aqueous dispersions.

The invention is explained in more detail by the examples, without limiting it as a result.

EXAMPLES

A Preparation of the Monomers

Example 1

Synthesis of 1,23-diethyltricosanedioate

A mixture of 10 ml of ethanol, 1.79 g of ethyl erucate, 0.079 mmol of palladium(II) acetate, 0.39 mmol of 1,2-bis[(di-tert-butylphosphino)methyl]benzene and 0.79 mmol of methanesulfonic acid was stirred in a pressurized reactor for 22 h at 90° C. and a carbon monoxide pressure of 20 bar. The reaction mixture was concentrated on a rotary evaporator at 200 mbar and 50° C. 5 ml of dichloromethane were then added. The mixture was filtered and concentrated on a rotary evaporator at atmospheric pressure and 50° C. The residue was recrystallized from ethanol. Yield 76% based on ethyl erucate used. According to the $^1$H NMR spectrum, >99% is 1,23-diethyltricosanedioate.

Comparative Example

A mixture of 10 ml of methanol, 1.79 g of methyl erucate (95%), 0.079 mmol of palladium(II) acetate, 0.39 mmol of 1,2-bis[(di-tert-butylphosphino)methyl]benzene and 0.79 mmol of methanesulfonic acid was stirred in a pressurized reactor for 22 h at 90° C. and a carbon monoxide pressure of 20 bar. The mixture comprises predominantly the non-carbonylated monocarboxylic acid methyl ester.

Example 2

Synthesis of 1,23-tricosanedicarboxylic Acid

In total, 55.2 mmol of KOH were added to a suspension of 20 ml of methanol and 4.5 mmol of 1,23-diethyltricosanedioate. The mixture was heated at reflux with stirring for 10 hours. The solvent was then removed in vacuo. 30 ml of water were added to the resulting white solid, and 6 N hydrochloric acid was used to acidify the mixture to pH=2. The mixture was filtered and the white solid was recrystallized from methanol. Yield 96% based on 1,23-diethyltricosanedioate used. According to the $^1$H NMR spectrum, >99% is 1,23-tricosanedicarboxylic acid.

Example 3

Synthesis of 1,23-tricosanediol (Route A)

2.3 mmol of 1,23-diethyltricosanedioate were dissolved in 10 ml of tetrahydrofuran. This solution was slowly added dropwise with stirring to a suspension of 5.2 mmol of lithium aluminum hydride in 10 ml of tetrahydrofuran. The mixture was heated at reflux with stirring for one hour and then stirred overnight at room temperature. With stirring, 0.2 ml of water, 0.2 ml of 15% strength aqueous NaOH solution, and 0.6 ml of water were slowly added in succession. The mixture was filtered at 40° C. The filtrate was evaporated on a rotary evaporator at 50° C. and 500 mbar. The residue was recrystallized from ethanol. Yield 80% based on 1,23-diethyltricosanedioate used. According to $^1$H NMR spectrum, >99% is 1,23-dihydroxytricosane.

Example 4

Synthesis of 1,23-tricosanediol (Route B)

A mixture of 40 ml of tetrahydrofuran, 5.6 mmol of 1,23-diethyltricosanedioate, 5.6 μmol of dichlorobis[2-(diphenylphosphino)ethylamine]ruthenium and 0.56 mmol of sodium methanolate were stirred in a pressurized reactor for 22 hours at 100° C. and a hydrogen pressure of 50 bar. The reaction mixture was filtered at 40° C. The filtrate was concentrated on a rotary evaporator at 50° C. and 500 mbar. The residue was recrystallized from toluene. Yield 78% based on 1,23-diethyltricosanedioate used.

B Polycondensations and Polycondensates

Example 5

Polyester (23,23)

In a 10 ml flask with tap, 1.4 mmol of 1,23-diethyltricosanedioate, 1.4 mmol of 1,23-dihydroxytricosane and 0.28 mmol of titanium tetrabutanolate were heated in the course of 17 h from 110° C. to 150° C. at 0.01 mbar. After cooling, a white solid was obtained.

Gel permeation chromatography (solvent 1,2,4-trichlorobenzene, 160° C., against linear polyethylene standards) revealed a molecular weight of $M_n$ $10^4$ g mol$^{-1}$ ($M_w/M_n$ 2). Differential heat flow calorimetry (DSC) reveals a peak melting point of $T_m$ 99° in the first and second heating curve, a crystallization temperature of 84° C., and a melt enthalpy of 180 J g$^{-1}$.

Example 6

Polyester (23,12)

In a 100 ml Schlenk with mechanical stirrer, 2.8 mmol of 1,23-diethyltricosanediolate and 1,12-dodecanediol were heated with 0.028 mmol of titanium tetrabutanolate in 0.1 ml of toluene from 100° C. to 220° C. over a period of 8 hours. Then, at 220° C. and 0.01 mbar, the mixture was stirred for 1 hour. After cooling, a white solid was obtained.

Differential heat flow calorimetry (DSC) reveals a peak melting point of $T_m$ 101° C. in the second heating curve, a crystallization temperature of $T_c$ 76° C. and a melt enthalpy of $\Delta H_m$ 156 J g$^{-1}$.

Example 7

Polyester (23,6)

In a 100 ml Schlenk with mechanical stirrer, 2.8 mmol of 1,23-diethyltricosanedioate and 1,6-hexanediol were heated with 0.028 mmol of titanium tetrabutanolate in 0.1 ml of toluene from 100° C. to 220° C. over a period of 8 hours. The mixture was then stirred at 220° C. and 0.01 mbar for 1 hour. After cooling, a white solid was obtained.

Differential heat flow calorimetry (DSC) reveals a peak melting point of $T_m$ 92° C. in the second heating curve, a crystallization temperature of $T_c$ 75° C. and a melt enthalpy of $\Delta H_m$ 145 J/g.

Example 8

Polyester (23,4)

In a 100 ml Schlenk with mechanical stirrer, 2.8 mmol of 1,23-diethyltricosanedioate and 1,4-butanediol were heated with 0.028 mmol of titanium tetrabutanolate in 0.1 ml of toluene from 100° C. to 200° C. over a period of 4 hours. The mixture was then stirred at 220° C. and for 8 hours and for a further hour at 220° C. and 0.01 mbar. After cooling, a white solid was obtained.

Differential heat flow calorimetry (DSC) reveals a peak melting point of $T_m$ 85° C. in the second heating curve, a crystallization temperature of $T_c$ 71° C. and a melt enthalpy of $\Delta H_m$ 172 J g$^{-1}$.

Example 9

Polyamide (23,23)

Tricosamethylenediamine tricosanedioate was produced in 9 ml of ethanol from 1.04 mmol of 1,23-diaminotricosane and 1.04 mmol of 1,23-tricosanedicarboxylic acid.

In a 100 ml Schlenk with mechanical stirrer, 1.04 mmol of tricosamethylenediamine tricosanedioate were heated with 0.037 mmol of 1,23-diaminotricosane from 120° C. to 210° C. under an argon atmosphere over a period of 3 hours and stirred at this temperature for 1.5 hours. Then, at 210° C., a vacuum of 1×10$^{-5}$ bar was applied for 17.5 hours. After cooling, a beige solid was obtained.

Differential heat flow calorimetry (DSC) revealed a peak melting point of $T_m$ 151° C. in the second heating curve, a crystallization temperature of $T_c$ 130° C. and a melt enthalpy of $\Delta H_m$ 88 J g$^{-1}$.

Example 10

Polyamide (12,23)

Dodecamethylenediamine tricosanedioate was prepared in 9 ml of ethanol from 1.43 mmol of 1,12-diaminododecane and 1.43 mmol of 1,23-tricosanedicarboxylic acid.

In a 100 ml Schlenk with mechanical stirrer, 1.43 mmol of dodecamethylenediamine tricosanedioate were heated with 0.045 mmol of 1,12-diaminododecane from 100° C. to 200°

C. under an argon atmosphere over a period of 5.5 hours and stirred at this temperature for 16.5 hours. Then, at 200° C., a vacuum of 1×10$^{-5}$ bar was applied for 4 hours. After cooling, a beige solid was obtained.

Differential heat flow calorimetry (DSC) reveals a peak melting point of $T_m$ 168° C. in the second heating curve, a crystallization temperature of $T_c$ 150° C. and a melt enthalpy of $\Delta H_m$ 121 J g$^{-1}$.

Example 11

Polyamide (23,19)

Tricosamethylenediamine nonadecanedioate was produced in 8 ml of ethanol from 1.06 mmol of 1,23-diaminotricosane and 1.06 mmol of 1,19-nonadecanedicarboxylic acid.

In a 100 ml Schlenk with mechanical stirrer, 1.06 mmol of tricosamethylenediamine nonadecanedioate were heated from 100° C. to 230° C. under an argon atmosphere over a period of 4.5 hours and stirred at this temperature for 1.25 hours. Then, at 230° C., a vacuum of 1×10$^{-5}$ bar was applied for 16.5 hours. After cooling, a beige solid was obtained.

Differential heat flow calorimetry (DSC) reveals a peak melting point of $T_m$ 156° C. in the second heating curve, a crystallization temperature of $T_c$ 132° C. and a melt enthalpy of $\Delta H_m$ 85 J g$^{-1}$.

The invention claimed is:

1. A method for producing saturated or unsaturated α,ω-dicarboxylic acids or esters having in each case 2n+3 carbon atoms in the acid moiety, where n is ≥10, comprising the step of a hydroxy or alkoxycarbonylation of a mono- or polyunsaturated fatty acid ester having 2n+2 carbon atoms in the acid moiety, where n is ≥10, in the presence of a catalyst comprising at least one palladium compound and at least one phosphane, at a temperature in the range from 85 to 120° C. and a pressure from 3 to 80 atm and where the alkoxy compound is a $C_2$-$C_{36}$-alcohol.

2. The method according to claim 1, wherein the catalyst comprises a palladium Op salt and 1,2-bis[(di-tert-dutylphosphino)methyl]benzene.

3. The method according to claim 1, where the fatty acid ester is an ester of erucic acid.

4. The method according to claim 1, wherein temperature in the range of 85 to 100° C.

5. The method according to claim 1, wherein the pressure from 10 to 40 atm.

6. The method according to claim 4, wherein the pressure from 10 to 40 atm.

* * * * *